(12) United States Patent
Hodgkinson

(10) Patent No.: US 9,010,610 B2
(45) Date of Patent: Apr. 21, 2015

(54) BUTTRESS RETENTION SYSTEM FOR LINEAR ENDOSTAPLERS

(71) Applicant: Covidien LP, Mansfield, MA (US)

(72) Inventor: Gerald Hodgkinson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/467,166

(22) Filed: Aug. 25, 2014

(65) Prior Publication Data

US 2014/0361067 A1     Dec. 11, 2014

Related U.S. Application Data

(63) Continuation of application No. 13/404,134, filed on Feb. 24, 2012, now Pat. No. 8,820,606.

(51) Int. Cl.
    *A61B 17/068*        (2006.01)
    *A61B 17/072*        (2006.01)

(52) U.S. Cl.
CPC ......... *A61B 17/07207* (2013.01); *A61B 17/072* (2013.01); *A61B 17/07292* (2013.01); *A61B 17/068* (2013.01); *A61B 2017/07257* (2013.01); *A61B 2017/07271* (2013.01)

(58) Field of Classification Search
CPC .................. A61B 17/068; A61B 17/07292
USPC .................. 227/176.1, 175.1, 19; 606/151
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |

(Continued)

FOREIGN PATENT DOCUMENTS

| | | |
|---|---|---|
| DE | 19924311 A1 | 11/2000 |
| EP | 0 327 022 A2 | 8/1989 |

(Continued)

OTHER PUBLICATIONS

European Search Report corresponding to EP 05 02 2585.3, completed Jan. 25, 2006 and mailed Feb. 3, 2006; (4 pp).

(Continued)

*Primary Examiner* — Michelle Lopez

(57) ABSTRACT

An end effector for use with a surgical stapler comprising a staple cartridge having a tissue contacting surface, a first side surface, and a second side surface opposite the first side surface, an anvil plate having a tissue contacting surface, a first side surface, and a second side surface opposite the first side surface, wherein the first and second side surfaces of each of the staple cartridge and anvil plate have overmolded zones, a buttress releasably disposed on the tissue contacting surfaces of each of the staple cartridge and the anvil plate, and a pair of sutures wherein each suture is bonded to the respective overmolded zones of the first and second side surfaces configured to retain the respective buttress atop the respective tissue contacting surfaces.

15 Claims, 5 Drawing Sheets

(56) References Cited

U.S. PATENT DOCUMENTS

| | | |
|---|---|---|
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,590,095 B1 | 7/2003 | Schleicher et al. |
| 6,592,597 B2 | 7/2003 | Grant et al. |
| 6,605,294 B2 | 8/2003 | Sawhney |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,009,034 B2 | 3/2006 | Pathak et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |

(56) References Cited

U.S. PATENT DOCUMENTS

| | | | |
|---|---|---|---|
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,038,045 B2 | 10/2011 | Bettuchi et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,408,440 B2 | 4/2013 | Olson et al. |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,668,129 B2 | 3/2014 | Olson |
| 8,684,250 B2 | 4/2014 | Bettuchi et al. |
| 8,820,606 B2 * | 9/2014 | Hodgkinson ............. 227/176.1 |
| 2002/0028243 A1 | 3/2002 | Masters |
| 2002/0086990 A1 | 7/2002 | Kumar et al. |
| 2002/0091397 A1 | 7/2002 | Chen |
| 2003/0065345 A1 | 4/2003 | Weadock |
| 2003/0078209 A1 | 4/2003 | Schmidt |
| 2003/0083676 A1 | 5/2003 | Wallace |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0149073 A1 | 7/2005 | Arani et al. |
| 2005/0154093 A1 | 7/2005 | Kwon et al. |
| 2006/0004407 A1 | 1/2006 | Hiles et al. |
| 2006/0008505 A1 | 1/2006 | Brandon |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0237741 A1 | 10/2007 | Figuly et al. |
| 2007/0237742 A1 | 10/2007 | Figuly et al. |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |

(56) References Cited

U.S. PATENT DOCUMENTS

| | | |
|---|---|---|
| 2008/0169333 A1 | 7/2008 | Shelton et al. |
| 2008/0194805 A1 | 8/2008 | Vignon et al. |
| 2008/0200949 A1 | 8/2008 | Hiles et al. |
| 2008/0214695 A1 | 9/2008 | Pathak et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0220560 A1 | 9/2009 | Wan et al. |
| 2009/0263441 A1 | 10/2009 | McKay |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0096481 A1 | 4/2010 | Hull et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089375 A1 | 4/2011 | Chan et al. |
| 2011/0293690 A1 | 12/2011 | Griffin et al. |
| 2012/0156289 A1 | 6/2012 | Blaskovich et al. |
| 2012/0187179 A1 | 7/2012 | Gleiman |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0181031 A1 | 7/2013 | Olson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |

FOREIGN PATENT DOCUMENTS

| | | |
|---|---|---|
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 A1 | 8/2009 |
| EP | 2 090 244 A2 | 8/2009 |
| EP | 2 090 252 A2 | 8/2009 |
| EP | 2 198 787 A1 | 6/2010 |
| EP | 2 236 098 A2 | 10/2010 |
| EP | 2 311 386 A2 | 4/2011 |
| EP | 2 462 880 A2 | 6/2012 |
| EP | 2 517 637 A1 | 10/2012 |
| EP | 2 620 106 A2 | 7/2013 |
| EP | 2 630 922 A1 | 8/2013 |
| EP | 2 644 125 A2 | 10/2013 |
| JP | 2000-166933 A | 6/2000 |
| JP | 2002-202213 A | 7/2002 |
| JP | 2007-124166 A | 5/2007 |
| WO | 90/05489 A1 | 5/1990 |
| WO | 95/16221 A1 | 6/1995 |
| WO | 96/22055 A1 | 7/1996 |
| WO | 97/01989 A1 | 1/1997 |
| WO | 97/13463 A1 | 4/1997 |
| WO | 98/17180 A1 | 4/1998 |
| WO | 99/45849 A1 | 9/1999 |
| WO | 03/088845 A2 | 10/2003 |
| WO | 03082126 A1 | 10/2003 |
| WO | 03/094743 A1 | 11/2003 |
| WO | 03/105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |

(56) References Cited

FOREIGN PATENT DOCUMENTS

| WO | 2010075298 A2 | 7/2010 |
|---|---|---|
| WO | 2011143183 A2 | 11/2011 |
| WO | 2012044848 A1 | 4/2012 |

OTHER PUBLICATIONS

European Search Report corresponding to EP 06 00 4598, completed Jun. 22, 2006; (2 pp).
European Search Report corresponding to EP 06 01 6962.0, completed Jan. 3, 2007 and mailed Jan. 11, 2007; (10 pp).
International Search Report corresponding to International Application No. PCT/US2005/036740, completed Feb. 20, 2007 and mailed Mar. 23, 2007; (8 pp).
International Search Report corresponding to International Application No. PCT/US2007/022713, completed Apr. 21, 2008 and mailed May 15, 2008; (1 p).
International Search Report corresponding to International Application No. PCT/US2008/002981, completed Jun. 9, 2008 and mailed Jun. 26, 2008; (2 pp).
European Search Report corresponding to EP 08 25 1779, completed Jul. 14, 2008 and mailed Jul. 23, 2008; (5 pp).
European Search Report corresponding to EP 08 25 1989.3, completed Mar. 11, 2010 and mailed Mar. 24, 2010; (6 pp).
European Search Report corresponding to EP 10 25 0639.1, completed Jun. 17, 2010 and mailed Jun. 28, 2010; (7 pp).
European Search Report corresponding to EP 10 25 0715.9, completed Jun. 30, 2010 and mailed Jul. 20, 2010; (3 pp).
European Search Report corresponding to EP 05 80 4382.9, completed Oct. 5, 2010 and mailed Oct. 12, 2010; (3 pp).
European Search Report corresponding to EP 10 25 1437.9, completed Nov. 22, 2010 and mailed Dec. 16, 2010; (3 pp).
European Search Report corresponding to EP 09 25 2897.5, completed Feb. 7, 2011 and mailed Feb. 15, 2011; (3 pp).
European Search Report corresponding to EP 10 25 0642.5, completed Mar. 25, 2011 and mailed Apr. 4, 2011; (4 pp).
European Search Report corresponding to EP 11 18 8309.6, completed Dec. 15, 2011 and mailed Jan. 12, 2012; (3 pp).
European Search Report corresponding to EP 12 15 2229.6, completed Feb. 23, 2012 and mailed Mar. 1, 2012; (4 pp).
European Search Report corresponding to EP 12 15 0511.9, completed Apr. 16, 2012 and mailed Apr. 24, 2012; (7 pp).
European Search Report corresponding to EP 12 15 2541.4, completed Apr. 23, 2012 and mailed May 3, 2012; (10 pp).
European Search Report corresponding to EP 12 16 5609.4, completed Jul. 5, 2012 and mailed Jul. 13, 2012; (8 pp).
European Search Report corresponding to EP 12 15 8861.0, completed Jul. 17, 2012 and mailed Jul. 24, 2012; (9 pp).
European Search Report corresponding to EP 12 16 5878.5, completed Jul. 24, 2012 and mailed Aug. 6, 2012; (8 pp).
Extended European Search Report corresponding to EP 12 19 1035.0, completed Jan. 11, 2013 and mailed Jan. 18, 2013; (7 pp).
Extended European Search Report corresponding to EP 12 18 6175.1, completed Jan. 15, 2013 and mailed Jan. 23, 2013; (7 pp).
Extended European Search Report corresponding to EP 12 19 1114.3, completed Jan. 23, 2013 and mailed Jan. 31, 2013; (10 pp).
Extended European Search Report corresponding to EP 12 19 2224.9, completed Mar. 14, 2013 and mailed Mar. 26, 2013; (8 pp).
Extended European Search Report corresponding to EP 12 19 6904.2, completed Mar. 28, 2013 and mailed Jul. 26, 2013; (8 pp).
Extended European Search Report corresponding to EP 12 19 6911.7, completed Apr. 18, 2013 and mailed Apr. 24, 2013; (8 pp).
Extended European Search Report corresponding to EP 07 00 5842.5, completed May 13, 2013 and mailed May 29, 2013; (7 pp).
Extended European Search Report corresponding to EP 12 19 8776.2, completed May 16, 2013 and mailed May 27, 2013; (8 pp).
Extended European Search Report corresponding to EP 12 19 8749.9, completed May 21, 2013 and mailed May 31, 2013; (8 pp).
Extended European Search Report corresponding to EP 13 15 6297.7, completed Jun. 4, 2013 and mailed Jun. 13, 2013I; (7 pp).
Extended European Search Report corresponding to EP 13 17 3985.6, completed Aug. 19, 2013 and mailed Aug. 28, 2013; (6 pp).
Extended European Search Report corresponding to EP 13 17 3986.4, completed Aug. 20, 2013 and mailed Aug. 29, 2013; (6 pp).
Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).

* cited by examiner

BUTTRESS RETENTION SYSTEM FOR LINEAR ENDOSTAPLERS

CROSS-REFERENCE TO RELATED APPLICATIONS

The present application is a Continuation Application claiming the benefit of and priority to U.S. patent application Ser. No. 13/404,134, filed Feb. 24, 2012, now U.S. Pat. No. 8,820,606, the entire disclosure of which is incorporated by reference herein.

BACKGROUND

1. Technical Field

The present disclosure relates to a surgical stapling apparatus and, more particularly, to a surgical stapling apparatus including an anchor member or members affixed to at least one of an anvil plate and staple cartridge to secure one or more buttresses thereto.

2. Background of Related Art

Surgical stapling instruments that are used to sequentially or simultaneously apply one or more rows of fasteners to join segments of body tissues are well known in the art. The fasteners are typically in the form of surgical staples but two part polymeric fasteners can also be utilized. Such devices generally include a pair of jaws to clamp the body tissues between such jaws. Typically, one of the jaw members includes a staple cartridge which accommodates a plurality of staples arranged in one or more rows while the other jaw member has an anvil plate that defines a surface for forming the staple legs as the staples are driven from the staple cartridge against the anvil.

Certain surgical staplers have elongate jaws that apply linear rows of staples to tissue. When such a stapling instrument is actuated, a longitudinally translating actuation member contacts staple drive members in one of the jaws which in turn acts upon staple pushers to sequentially eject the staples from the staple cartridge. For example, longitudinally traveling cam bar members can be used to interact with the staple drive members. Alternatively, the staples can be driven simultaneously. A blade can travel between the staple rows to longitudinally cut and/or open the stapled tissue between the rows of staples. Such instruments are disclosed, for example, in U.S. Pat. No. 3,079,606 and U.S. Pat. No. 3,490,675.

When stapling relatively thin or fragile tissues, it may be important to effectively seal the staple line against air or fluid leakage. Additionally, it may be necessary to reinforce the staple line against the tissue to prevent tears in the tissue or pulling of the staples through the tissue. One method of preventing tears or pull through involves the placement of a biocompatible fabric reinforcing material, or a "buttress," between the staple and the underlying tissue. In this method, a layer of buttress is placed against the tissue and the tissue is stapled in a conventional manner. Surgical staplers utilizing pins or clips to temporarily connect buttresses to each of the jaws of the staplers, i.e., one disposed on the staple cartridge and the other on the anvil plate, are known.

The present application discloses a retention system for securing one or more buttresses to the jaws of the stapler. The retention system allows the buttresses to be secured to a tissue contacting surface of the staple cartridge and anvil plate. This retention system reduces manufacturing costs associated with surgical staplers. Further, this retention system diminishes the likelihood of premature suture release during assembly, packing or firing. Fewer design and testing constraints will be imposed as less precision is required to achieve acceptable functioning retention elements.

SUMMARY

The present application discloses an end effector for use with a surgical stapler, the end effector comprising a staple cartridge assembly having a tissue contacting surface, a first side surface, and a second side surface opposite the first side surface, an anvil assembly having a tissue contacting surface, a first side surface, and a second side surface opposite the first side surface, the staple cartridge assembly and anvil assembly having proximal and distal attachment zones. A buttress is releasably disposed on the tissue contacting surfaces of each of the staple cartridge assembly and anvil assembly, and a pair of anchor members are affixed to the attachment zones of each of the staple cartridge assembly and anvil assembly and are configured to retain the respective buttress material atop the respective tissue contacting surfaces. In certain embodiments, one of the staple cartridge assembly and anvil assembly has a buttress material releasably attached thereto.

In certain embodiments, the first and second side surfaces of each of the staple cartridge assembly and anvil assembly have overmolded zones, a buttress releasably disposed on the tissue contacting surfaces of each of the staple cartridge and the anvil plate, and a pair of anchor members wherein each anchor member is bonded to the respective overmolded zones of the first and second side surfaces configured to retain the respective buttress atop the respective tissue contacting surfaces. Preferably, the overmolded zones are made from polymeric material. Alternatively, attachment zones may be composed of press fit parts that are attached to the anvil assembly, or attachment zones may be composed of molded features integral to the cartridge assembly. The anchor member is desirably a polymeric suture. A proximal suture is positioned along a proximal portion of each of the staple cartridge assembly and anvil assembly, and a distal suture is positioned along a distal portion of each of the staple cartridge assembly and the anvil assembly. A first end of the proximal suture couples to the overmolded zone of the first side surface and a second end of the proximal suture couples to the overmolded zone of the second side surface. The proximal suture passes transversely across a proximal portion of the buttresses of each of the staple cartridge assembly and anvil assembly. Similarly, a first end of the distal suture couples to the overmolded zone of the first side surface and a second end of the distal suture couples to the overmolded zone of the second side surface. The distal suture passes transversely across the distal portion of the buttresses of each of the staple cartridge assembly and anvil assembly.

The staple cartridge assembly and the anvil assembly have a central longitudinal slot configured to enable a passage of a knife blade therethrough. The proximal suture is positioned distally from a proximal end of the central longitudinal slot on each of the staple cartridge assembly and anvil assembly. The distal suture is positioned proximally from a distal end of the central longitudinal slot on each of the staple cartridge assembly and anvil assembly.

In a further aspect, an end effector for use with a surgical stapler, the end effector comprising: a staple cartridge having a tissue contacting surface, a first side surface and a second side surface opposite the first side surface, wherein the first and second side surfaces have overmolded zones disposed near a proximal and distal portion thereof; and an anvil plate having a tissue contacting surface, a first side surface and a second side surface opposite the first side surface, wherein the first and second side surfaces have overmolded zones disposed near a proximal and distal portion thereof. A buttress material is releasably disposed on the tissue contacting surfaces of each of the staple cartridge and the anvil plate. The end effector has a pair of sutures, wherein each suture is bonded to the respective overmolded zones of the first and second side surfaces of each of the staple cartridge and anvil plate.

A proximal suture may be positioned along the proximal portion of each of the staple cartridge and anvil plate, and a distal suture may be positioned along the distal portion of each of the staple cartridge and the anvil plate. A first end of the proximal suture may couple to the overmolded zone of the first side surface and a second end of the proximal suture may couple to the overmolded zone of the second side surface such that the proximal suture passes transversely across a proximal portion of the buttresses of each of the staple cartridge and anvil plate. A first end of the distal suture may couple to the overmolded zone of the first side surface and a second end of the distal suture may couple to the overmolded zone of the second side surface such that the distal suture passes transversely across the distal portion of the buttresses of each of the staple cartridge and anvil plate.

In certain embodiments, the staple cartridge and the anvil plate have a central longitudinal slot configured to enable passage of a knife blade therethrough. The proximal suture may be positioned distally from a proximal end of the central longitudinal slot on each of the staple cartridge and anvil plate.

The distal suture may be positioned proximally to a distal end of the central longitudinal slot on each of the staple cartridge and anvil plate.

DESCRIPTION OF THE DRAWINGS

Various embodiments of the presently disclosed interlocking buttress retention systems are disclosed herein with reference to the drawings, wherein.

DETAILED DESCRIPTION OF EMBODIMENTS

Embodiments of the presently disclosed buttress retention method for linear endostaplers will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
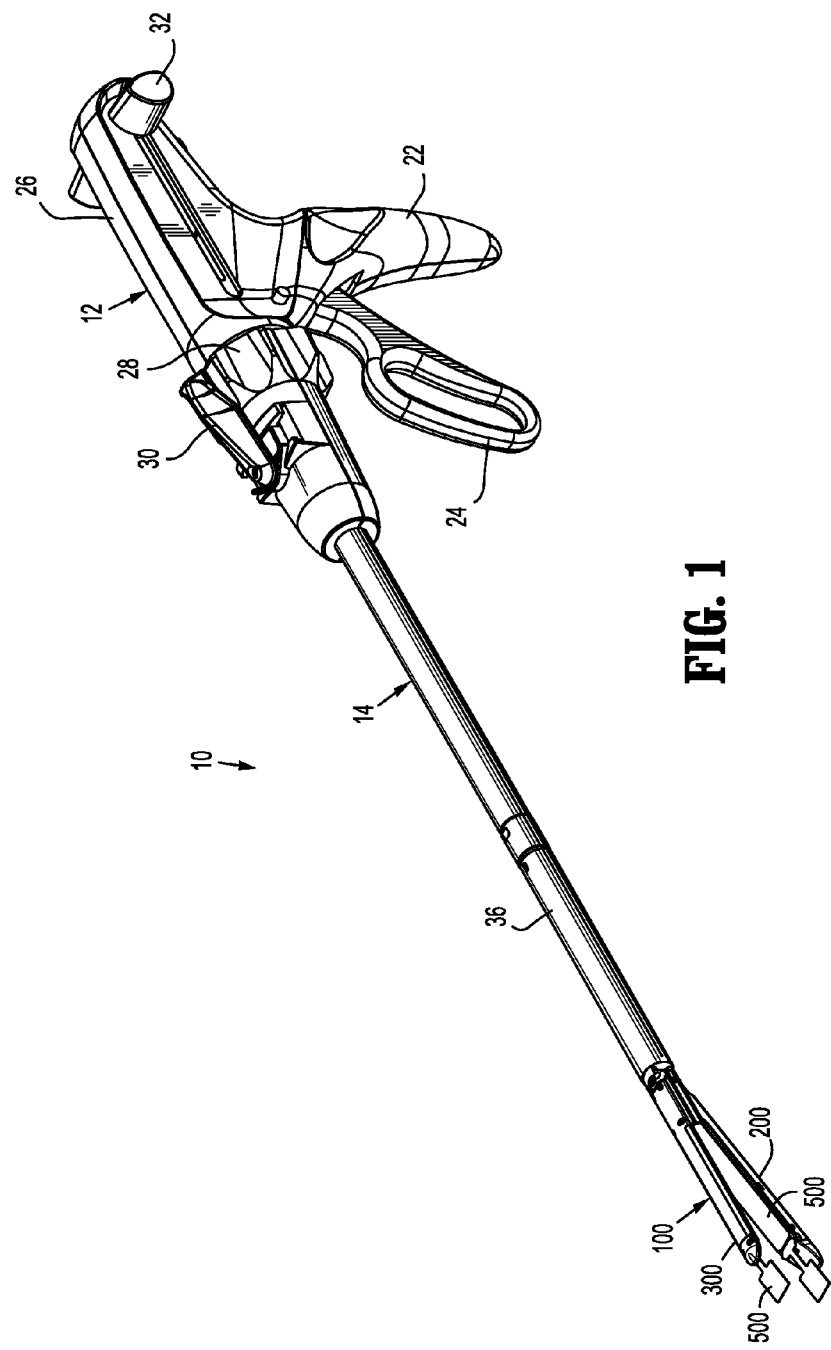
FIG. 1 is a perspective view of a surgical stapling apparatus according to an embodiment of the present disclosure.

Referring now to FIG. 1, there is disclosed a linear surgical stapling instrument or surgical stapler 10 for use in stapling tissue and applying layers of buttress material between the staples and underlying tissue. An exemplary example of this type of surgical stapling instrument is disclosed in U.S. Pat. No. 7,128,253, the entire disclosure of which is incorporated by reference herein.

Surgical stapler 10 generally includes a handle 12 having an elongate tubular member 14 extending distally from handle 12. An end effector 100 is secured on the distal end of elongate tubular member 14. End effector 100 includes a cartridge assembly 200 housing a plurality of surgical fasteners or staples 223 (see FIG. 2) and an anvil assembly 300 movably secured in relation to cartridge assembly 200. Handle assembly 12 includes a stationary handle member 22, a movable handle member 24, and a barrel portion 26. An articulation lever 30 is mounted on the forward end of barrel portion 26 adjacent rotatable member 28 to facilitate articulation of end effector 100. A pair of knobs 32 are movably positioned along barrel portion 26. Knobs 32 are advanced distally to approximate or close cartridge and/or anvil assembly 200, 300, and retracted proximally to unapproximate or open cartridge and/or anvil assembly 200, 300. Actuation of movable handle member 24 applies lines of staples 223 to tissue. In order to properly orient cartridge and anvil assembly 200, 300 relative to the tissue to be stapled, surgical stapling apparatus 10 is additionally provided with a rotatable member 28 on the forward end of barrel portion 26. Rotation of rotatable member 28 relative to handle assembly 12 rotates elongate body 14 and loading unit 100 relative to handle assembly 12 so as to properly orient cartridge assembly 200 and anvil assembly 300 relative to the tissue to be stapled.

One or more buttresses are attached to the cartridge assembly, the anvil assembly, or both. For example, the cartridge assembly 200 is provided with a cartridge buttress 500a and anvil assembly 300 is provided with an anvil buttress 500b in the manners described in more detail hereinbelow. A cartridge buttress retention system 250 (see FIG. 3) is provided to releasably secure cartridge buttress 500a to staple cartridge assembly 200. Likewise, an anvil buttress retention system 340 (see FIG. 4) is provided to releasably secure anvil buttress 500b to anvil assembly 300. Cartridge buttress 500a and anvil buttress 500b and are provided to reinforce and seal staple lines applied to tissue by surgical stapler 10.

The buttresses 500a, 500b may be made from any biocompatible natural or synthetic material. The material from which the buttresses 500a, 500b are formed may be bioabsorbable or non-bioabsorbable. It should be understood that any combination of natural, synthetic, bioabsorbable and non-bioabsorbable materials may be used to form the buttress material. The buttresses 500a, 500b may be porous or non-porous, combination of porous and non-porous layers. The non-porous buttresses 500a, 500b may be utilized to retard or prevent tissue ingrowth from surrounding tissues thereby acting as an adhesion barrier and preventing the formation of unwanted scar tissue. The buttress materials may be provided in the form of a sheet, a non-woven material, felt, mesh, foam or other form.

Additional exemplary materials for surgical buttresses 500a, 500b for use with the surgical stapling devices disclosed herein are set forth in commonly assigned U.S. Pat. Nos. 5,542,594; 5,908,427; 5,964,774; and 6,045,560, and commonly assigned U.S. Application Publication Nos. 2006/0085034, filed on Apr. 20, 2006; and 2006/0135992, filed on Jun. 22, 2006, the entire contents of each of which is incorporated herein by reference. Bio-absorbable polymers, non-bioabsorbable polymers, biologically appropriate metals, tissue-derived materials and composites thereof may be used.

Figure 2:
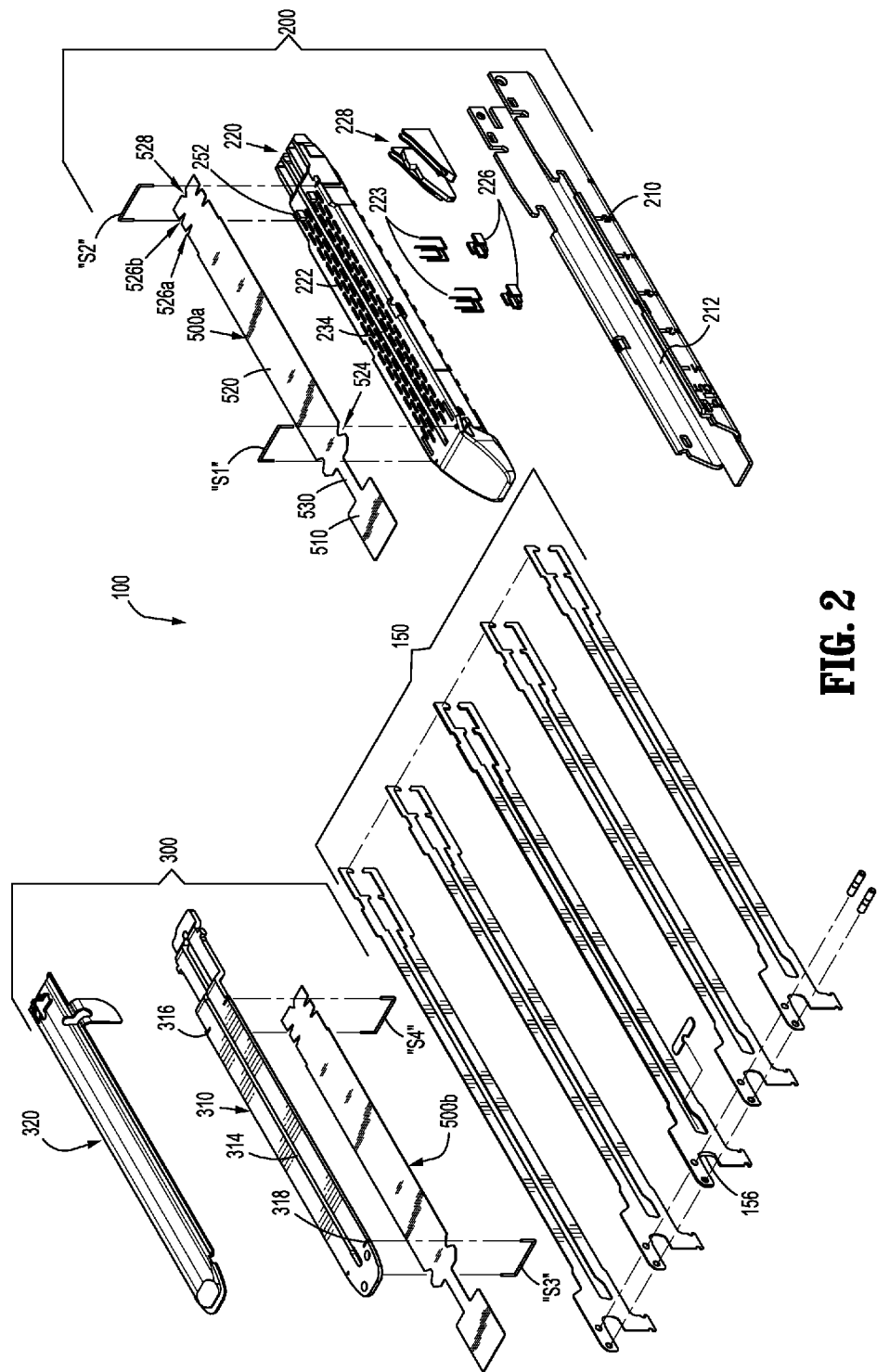
FIG. 2 is a top, exploded, perspective view of a distal end of the surgical stapling apparatus of FIG. 1.

As seen in FIG. 2, cartridge assembly 200 includes a carrier 210 defining an elongated support channel 212. Elongated support channel 212 of carrier 210 is dimensioned and configured to selectively receive a staple cartridge 220 therein. Staple cartridge 220 includes retention slots 222 formed therein for receiving a plurality of fasteners 223 and pushers 226. A central longitudinal slot 234 is formed in and extends along the length of staple cartridge 220 to facilitate passage of knife blade 156 of drive bar 150 therethrough. During operation of surgical stapler 10, actuation sled 228 translates through staple cartridge 220 to advance the cam wedges into sequential contact with pushers 226, to cause pushers 226 to translate vertically within retention slots 222 and urge staples 223 from slots 222 into staple forming cavities of anvil plate 310 of anvil assembly 300.

Cartridge buttress 500a of cartridge assembly 200 is operatively and releasebly secured to a tissue contacting surface of staple cartridge 220, by cartridge buttress retention system 250 wherein anchor members, which may comprise sutures "S1, S2," overlie the tissue contacting surface of the staple cartridge. In certain embodiments, the sutures overlie retention slots 222 and/or at least a portion of a length of longitudinal slot 234. A first anchor member or suture "S1" is affixed, as described in further detail hereinbelow, to staple cartridge 220 of the cartridge assembly and around/over distal portion of cartridge buttress 500a, and a second anchor member or suture "S2" is affixed to staple cartridge 220 around/over proximal portion of cartridge buttress 500a. Other anchor members may be used, such as straps, sheets, wires, cables, threads, rods, etc.

Figure 3:
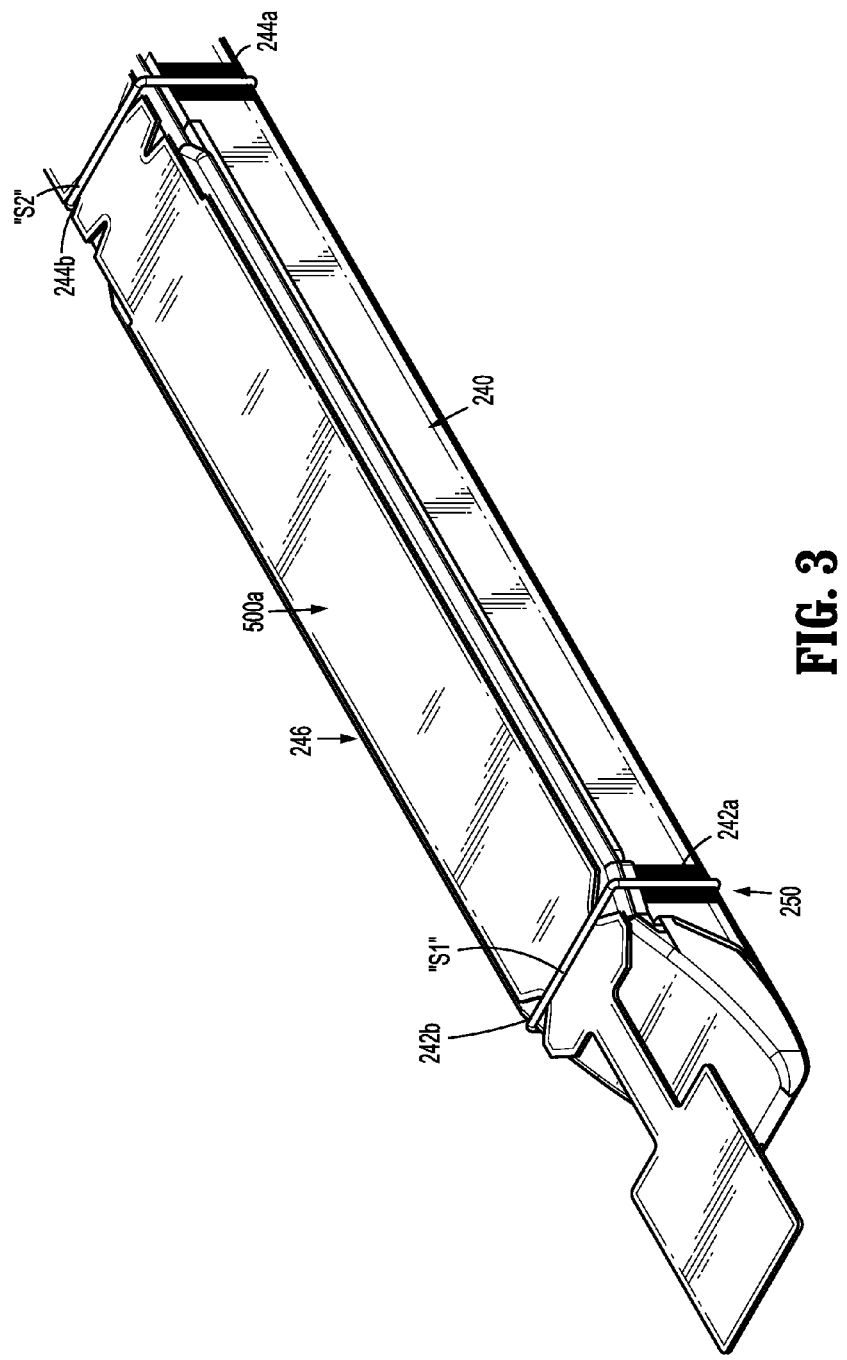
FIG. 3 is a perspective view of a cartridge assembly of FIG. 2, illustrating a cartridge buttress material secured thereto.

As best seen in FIG. 3, cartridge assembly 200 is shown with cartridge buttress 500a affixed by cartridge buttress retention system 250. Cartridge buttress 500a is positioned on the tissue contacting surface of staple cartridge 220. A first end of each anchor member or suture "S1, S2" is anchored or fixed to the staple cartridge assembly, and the second end of each suture is anchored or fixed to a second side surface of the staple cartridge assembly at attachment zones. For example, the first side surface 240 and second side surface of staple cartridge 220 have respective distal and proximal overmolded zones 242a, 244a, provided near the distal and proximal portions of staple cartridge 220. A second end of each suture "S1, S2" passes transversely across respective distal and proximal portions of cartridge buttress 500a and is anchored or fixed to a second side surface 246, opposite first side surface 240, at respective distal and proximal overmolded zones 242b, 244b, provided near the distal and proximal portions of staple cartridge 220. In this manner, sutures "S1, S2" are bonded to the overmolded zones and thus secure cartridge buttress 500a underneath to the tissue contacting surface of staple cartridge 220.

With reference again to FIG. 2, anvil assembly 300 includes an anvil plate 310 having a plurality of staple deforming pockets/cavities 310a (see FIG. 4) and a cover plate 320 secured to a top surface of anvil plate 310. Anvil assembly 300 further includes a knife blade 330 operatively interposed within the cavity defined between anvil plate 310 and cover plate 320.

Similar to cartridge buttress 500a, anvil buttress 500b may be operatively secured to a tissue contacting surface of anvil plate 310, by anvil buttress retention system 340. For example, sutures "S3, S4," overlie anvil pockets 310a and/or at least a portion of a length of longitudinal slot 314. A third suture "S3" is affixed to the anvil plate 310 around/over distal portion of anvil buttress 500b, and a fourth suture "S4" is affixed to anvil plate 310 around/over proximal portion of anvil buttress 500b.

Figure 4:
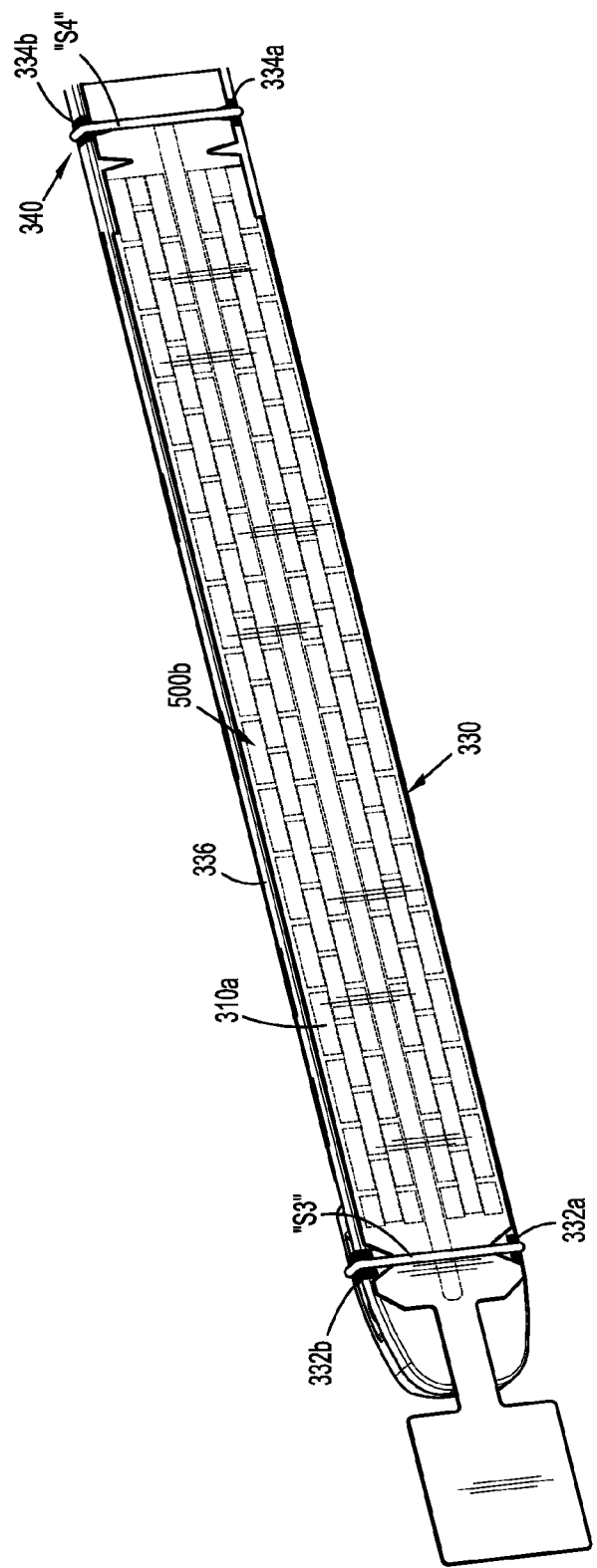
FIG. 4 is a perspective view of an anvil assembly of FIG. 2, illustrating an anvil buttress material secured thereto.

As shown in FIG. 4, anvil assembly 300 is shown with anvil buttress 500b affixed by anvil buttress retention system 340. Anvil buttress 500b is positioned on the tissue contacting surface of anvil plate 310. A first end of each suture "S3, S4" is anchored or fixed to a first side surface 330 of anvil plate 310 extending from the tissue contacting surface, at respective distal and proximal overmolded zones 332a, 334a, provided near the distal and proximal portions of anvil plate 310.

A second end of each suture "S3, S4" passes transversely across respective distal and proximal portions of anvil buttress 500b and is anchored or fixed to a second side surface 336, opposite first side surface 330, at respective distal and proximal overmolded zones 332b, 334b, provided near the distal and proximal portions of anvil plate 310. In this manner, sutures "S3, S4" are bonded to the overmolded zones and thus secure anvil buttress 500b underneath to the tissue contacting surface of anvil plate 310.

Bonding between the sutures and the overmolded zones of the cartridge buttress retention system and the anvil buttress retention system may be achieved by ultrasonic welding, laser welding, solvent welding, heat pressing, or by other similar methods known in the art of plastic to plastic bonding. It is contemplated that the overmolded zones are made of biocompatible plastic to which the sutures may optimally bond by the chosen bonding method. The overmolded plastic zones may be textured or grooved to accept the sutures and to promote optimal bonding. Alternatively, attachment zones may be composed of press fit parts that are attached to the anvil assembly, or attachment zones may be composed of molded features integral to the cartridge assembly.

Cartridge and anvil buttresses 500 are shown having a uniform profile. An example of this type of buttress is disclosed in U.S. Patent Publication No. 2011/0089220 filed on May 21, 2011, the entire disclosure of which is incorporated by reference herein. The buttresses include a head portion 510, a body portion 520, and a neck portion 530 interconnecting head portion and body portion. Body portion 520 defines a pair of opposing distal recesses 524 on transverse edges near a distal portion thereof. The pair of opposing distal recesses 524 are utilized to secure the body portion to a distal portion of each of the anvil plate and the staple cartridge.

Similarly, body portion 520 further defines a two pairs of opposing proximal recesses 526a, 526b on transverse edges near a proximal portion thereof. The pair of proximal recesses 526, 526b secure the body portion to a proximal portion of each of the anvil plate and the staple cartridge. The two pairs of proximal recesses allow the buttresses to accommodate various types of profiles of the anvil and cartridge assemblies. While the buttresses have been shown herein having a specific shape and design, it will be appreciated by those skilled in the art, that the buttresses may have various shapes to secure to the tissue contacting surfaces of various anvil and cartridge assemblies.

In operation, with end effector 100 coupled to a distal end of elongated body 14 of surgical stapling apparatus 10, and with cartridge and anvil buttresses 500a, 500b pre-loaded onto cartridge assembly 200 and anvil assembly 300, respectively, surgical stapling apparatus 10 is used in accordance with methods known by those skilled in the art. Once cartridge assembly 200 and anvil assembly 300 are clamped onto tissue, surgical stapling apparatus 10 is fired. In firing surgical stapling apparatus 10, drive bar 150 is advanced from a proximal-most position to a distal-most position of end effector 100. In so doing, knife blade 156 of drive bar 150 enters notch 528 of buttresses 500a, 500b thereby facilitating the dividing of buttresses 500a, 500b and reducing any incidents of pushing or bunching-up of buttresses 500a, 500b by blade 156. As drive bar 150 begins to travel distally, knife blade 156 substantially simultaneously cuts through a central section of the proximal sutures "S2, S4" of cartridge assembly 200 and anvil assembly 300, thereby respectively freeing the proximal ends of cartridge and anvil buttresses 500a, 500b therefrom. As knife blade 156 is moved distally, knife blade 156 slices or cuts longitudinally through both cartridge buttress 500a and anvil buttress 500b, thereby dividing the buttresses 500a, 500b substantially in half.

Additionally, as drive bar 150 approaches the distal-most position, drive bar 150 and/or knife blade 156 engage sutures "S1, S3" and sever distal sutures "S1 or S3" and thus release a distal end of buttresses 500a, 500b. In certain embodiments, a separate blade is mounted in the staple cartridge assembly and/or anvil assembly for cutting the anchor member or suture.

Figure 5:
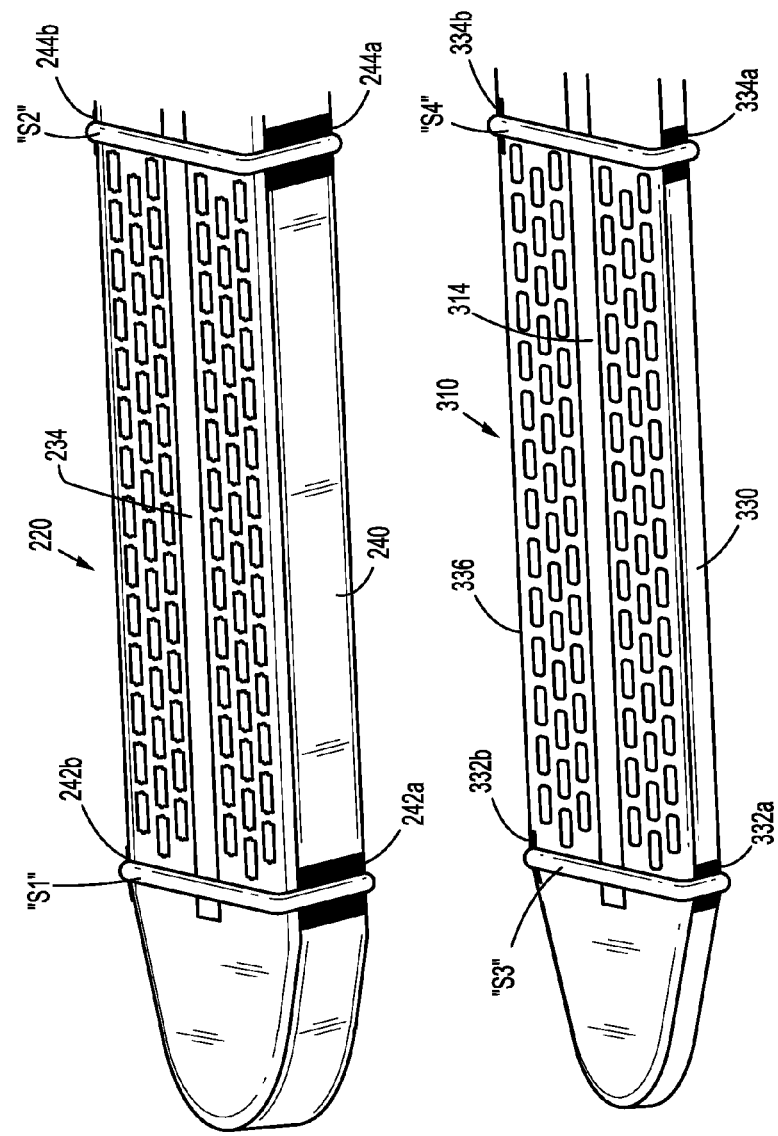
FIG. 5 is a perspective view of a cartridge assembly and an anvil assembly, illustrating sutures affixed thereto.

Referring to FIG. 5, staple cartridge 220 and anvil plate 310 are shown with the respective sutures affixed thereto without the buttresses. The sutures of cartridge assembly 200 and anvil assembly 300 are selectively positioned such that proximal sutures "S2, S4" are located distally from a proximal end of longitudinal slots 234, 314. Similarly, distal sutures "S1, S3" are located proximally from a distal end of longitudinal slots 234, 314. This allows knife blade 156 (FIG. 2) to sever proximal sutures "S2, S4" and distal sutures "S1, S3" as knife blade 156 translates along longitudinal slots 234, 314.

In certain other embodiments, the anchor member is welded, glued, or otherwise attached to the staple cartridge assembly and/or anvil assembly without the use of the overmolded material. For instance, attachment zones may be composed of press fit parts that are attached to the anvil assembly, or attachment zones may be composed of molded features integral to the cartridge assembly. In addition, in any of the embodiments discussed herein, the anchor member or members are permanently attached to the staple cartridge assembly and/or anvil assembly. However, in any of the embodiments disclosed herein, the anchor member or members can be temporarily attached to the staple cartridge assembly and/or anvil assembly so as to allow the anchor member to separate from the end effector to allow the buttress material to be released.

It will be understood that various modifications may be made to the embodiments of the presently disclosed buttress retention system for linear endostaplers. For example, the disclosed retention system is not limited to a stapling apparatus but may find application in other instruments and situations requiring material to be releasably retained on the surface of a surgical instrument. Therefore, the above description should not be construed as limiting, but merely as exemplifications of embodiments. Those skilled in the art will envision other modifications within the scope and spirit of the present disclosure.

What is claimed is:

1. An end effector for use with a surgical stapler, the end effector comprising:
   a staple cartridge having a tissue contacting surface, a first side surface and a second side surface opposite the first side surface, wherein the first and second side surfaces each have polymeric overmolded zones integrally formed with the staple cartridge and disposed near a proximal and a distal portion thereof;
   an anvil plate having a tissue contacting surface, a first side surface and a second side surface opposite the first side surface, wherein the first and second side surfaces each have polymeric overmolded zones integrally formed with the anvil plate and disposed near a proximal and a distal portion thereof;
   a buttress material releasably disposed on the tissue contacting surfaces of each of the staple cartridge and the anvil plate; and
   a pair of sutures configured to retain the respective buttress material atop the respective tissue contacting surfaces;
   wherein proximal sutures of the pairs of the staple cartridge and anvil plate sutures are positioned along the proximal portion of each of the staple cartridge and anvil plate, and wherein distal sutures of the pairs of sutures are positioned along the distal portion of each of the staple cartridge and the anvil plate;
   wherein each suture is bonded to the respective polymeric overmolded zone of the first and second side surfaces of each of the staple cartridge and anvil plate.

2. The end effector of claim 1, wherein at least one overmolded zone is textured.

3. The end effector of claim 1, wherein at least one overmolded zone defines at least one groove.

4. The end effector of claim 1, wherein each suture is a polymeric suture.

5. The end effector of claim 4, wherein each polymeric overmolded zone is chemically compatible with each polymeric suture.

6. The end effector of claim 1, wherein each suture bond is an ultrasonic weld, laser weld or solvent weld.

7. The end effector of claim 1, wherein the staple cartridge further includes a plurality of staple retaining slots.

8. The end effector of claim 1, wherein the staple cartridge further includes a central longitudinal extending knife slot.

9. The end effector of claim 8, wherein the distal suture on the staple cartridge is disposed proximal to the central longitudinal extending knife slot.

10. A staple cartridge configured for selective receipt in a jaw of a surgical stapler, the staple cartridge comprising:
    a tissue contacting surface defining a plurality of staple retaining slots and a central longitudinal extending knife slot; and
    a first side surface and a second side surface opposite the first side surface;
    wherein the first and second side surfaces each have polymeric overmolded zones integrally formed with the staple cartridge and disposed near a proximal and a distal portion thereof.

11. The staple cartridge of claim 10, wherein at least one overmolded zone is textured.

12. The staple cartridge of claim 10, wherein at least one overmolded zone defines at least one groove.

13. The staple cartridge of claim 10, further including a buttress releasably disposed on the tissue contacting surface of the staple cartridge.

14. The staple cartridge of claim 13, further including a pair of sutures traversing across the proximal and the distal portions of the staple cartridge, wherein the pair of sutures secure the buttress to the tissue contacting surface.

15. The staple cartridge of claim 14, wherein each suture is bonded to the respective polymeric overmolded zone of the first and second side surfaces of the staple cartridge.

* * * * *